United States Patent
Sun et al.

(10) Patent No.: US 12,217,498 B2
(45) Date of Patent: Feb. 4, 2025

(54) DEFECT INSPECTION SYSTEM HAVING HUMAN-MACHINE INTERACTION FUNCTION

(71) Applicants: KAPITO INC., Hsinchu (TW); Feng-Tso Sun, Hsinchu (TW); Yi-Ting Yeh, Hsinchu (TW); Feng-Yu Sun, Hsinchu (TW)

(72) Inventors: Feng-Tso Sun, Hsinchu (TW); Yi-Ting Yeh, Hsinchu (TW); Feng-Yu Sun, Hsinchu (TW); Jyun-Tang Huang, Hsinchu (TW); Po-Han Chou, Hsinchu (TW)

(73) Assignees: Kapito Inc., Hsinchu (TW); Feng-Tso Sun, Hsinchu (TW); Yi-Ting Yeh, Hsinchu (TW); Feng-Yu Sun, Hsinchu (TW)

(*) Notice: Subject to any disclaimer, the term of this patent is extended or adjusted under 35 U.S.C. 154(b) by 361 days.

(21) Appl. No.: 17/887,871

(22) Filed: Aug. 15, 2022

(65) Prior Publication Data
US 2023/0117656 A1  Apr. 20, 2023

(30) Foreign Application Priority Data
Oct. 20, 2021  (TW) .................................. 110138856

(51) Int. Cl.
*G06T 7/00*  (2017.01)
*G01N 21/88*  (2006.01)
(Continued)

(52) U.S. Cl.
CPC ....... *G06V 10/945* (2022.01); *G01N 21/8851* (2013.01); *G01N 33/367* (2013.01);
(Continued)

(58) Field of Classification Search
CPC ........ G06N 3/045; G06N 3/08; G06N 3/0464; G06N 3/044; G06N 3/048; G06N 3/084;
(Continued)

(56) References Cited

U.S. PATENT DOCUMENTS

| | | | | |
|---|---|---|---|---|
| 2014/0174127 A1* | 6/2014 | Dalstra | ................. | G01N 21/90 65/29.11 |
| 2020/0160497 A1* | 5/2020 | Shah | ......................... | G06T 7/70 |
| 2021/0383530 A1* | 12/2021 | Peleg | ....................... | G06N 3/06 |

FOREIGN PATENT DOCUMENTS

| | | |
|---|---|---|
| CN | 110148106 A | 8/2019 |
| CN | 111060514 A | 4/2020 |
| TW | M571486 U | 12/2018 |

* cited by examiner

*Primary Examiner* — Quan M Hua
(74) *Attorney, Agent, or Firm* — ANOVA LAW GROUP, PLLC

(57) ABSTRACT

A defect inspection system is disclosed, and comprises a linear light source, N number of cameras, a display device, a tag reader, and a modular electronic device, in which the linear light source, the cameras and the modular electronic device are used for conducting a defect inspection of an article. On the other hand, the display device, the tag reader and the modular electronic device are adopted for conducting in production of at least one labeled example. Therefore, the modular electronic device is allowed to apply a machine learning process to an image classifier under using a training dataset containing the labeled examples, thereby producing at least one new defect recognition model or updating the existing defect recognition model.

14 Claims, 7 Drawing Sheets

(51) Int. Cl.
  *G01N 33/36*  (2006.01)
  *G06T 7/246*  (2017.01)
  *G06V 10/44*  (2022.01)
  *G06V 10/94*  (2022.01)

(52) U.S. Cl.
  CPC .............. *G06T 7/001* (2013.01); *G06T 7/246* (2017.01); *G06V 10/443* (2022.01); *G01N 2021/8887* (2013.01); *G06T 2207/30164* (2013.01)

(58) Field of Classification Search
  CPC ........ G06N 3/04; G06N 3/0455; G06N 3/082; G06N 3/0895; G06V 10/82; G06V 10/26; G06V 10/267; G06V 10/44; G06V 10/764; G06V 10/774; G06V 30/274; G06V 10/25; G06V 10/751; G06V 20/46; G06V 20/53; G06T 7/194; G06T 2207/10016; G06T 2207/20081; G06T 2207/20084; G06T 7/215; G06T 7/11; G06T 7/136; G06T 2207/20076; G06T 2207/10024; G06T 7/254
  See application file for complete search history.

DEFECT INSPECTION SYSTEM HAVING HUMAN-MACHINE INTERACTION FUNCTION

CROSS-REFERENCE TO RELATED APPLICATION

This application claims the priority of Taiwan Patent Application No. 110138856, filed on Oct. 20, 2021, the content of which is incorporated by reference in its entirety.

TECHNICAL FIELD

The present invention relates to the technology field of machine vision inspection systems, and more particularly to a defect inspection system having human-machine interaction function.

BACKGROUND

It is well known that it is necessary to receive a defect inspection treatment for a woven article like fabric before being packed, and the defect inspection treatment is completed by an inspector through operating a fabric inspection machine (also called perching machine). Fabric manufacturer/supplier certainly know that, a conventional fabric inspection machine commonly includes: an unwinding unit, a fabric spreading unit and a winding unit, wherein the fabric spreading unit consists of a first feed roller, an inspection platform and a second feed roller. The first feed roller is disposed between the unwinding unit and the inspection platform, and is adjacent to a top side of the inspection platform. On the other hand, the second feed roller is disposed between the winding unit and the inspection platform, and is adjacent to a bottom side of the inspection platform.

A defect inspection treatment consists of multiple steps. In first step, the inspector stands at the front of an operation table, and then controls the actions of the unwinding unit, the first roller, the second roller, and the winding unit by operating a controller put on the operation table, so as to properly regulate a feeding speed and a winding speed of a fabric that is discharged from the winding unit and rewound by the unwinding unit. At the end of the foregoing first step, there is a segment of the fabric is laid out on the inspection platform. In second step, the inspector checks the appearance of the fabric segment spread on the inspection platform detailedly, and then operates the controller to stop the transmission of the fabric in case of there being at least one defect found. In third step, the inspector judges whether the defects in the fabric segment is repairable or not. If yes, the inspector repairs the defects; otherwise, the inspector patches a label on said defect. Eventually, the inspector restarts the transmission of the fabric by operating the controller, so as to make the fabric segment that has been received the defect inspection treatment be wound by the winding unit.

For accelerating the speed of the defect inspection treatment, the fabric manufacturer implements a fabric defect recognition system into the fabric inspection machine. The fabric defect system commonly includes at least one linear light source, N number of cameras and a modular electronic device coupled to the linear light source and the cameras. Particularly, the modular electronic device includes a processor and a memory, and the memory stores an application program. By such arrangements, when the fabric defect system works normally, the processor accesses the memory so as to execute the application program, thereby making the processor be configured for conducting a plurality of functions, including:

(i) controlling the light source to emit a detection light for irradiating a photographing region in case of the winding unit running to discharge the fabric by a fabric winding speed;

(ii) controlling the cameras to acquire an image frame from a segment of the fabric in the photographing region;

(iii) applying at least one image process to the image frame, so as to generate a fabric feature image; and (iv) extracting a plurality of defect features from the fabric feature image, and then determining whether there are existing any defects in the segment of the fabric by matching the plurality of defect features with a plurality of reference defect features.

Engineers skilled in research and development of machine vision inspection system certainly know that, there is a pre-trained defect recognition model stored/installed in the memory of the modular electronic device. As explained in more detail below, the pre-trained defect recognition model is produced after applying a machine learning process to an image classifier (or called image classification model) under using a training dataset, in which the image classifier including instructions which contains at least one mathematical algorithm. Moreover, the training dataset includes a plurality of first fabric images and a plurality of second fabric images, in which there is no defect features existing in said first fabric image, and each said second fabric image contains at least one kind of defect feature. It is worth noting that, the first fabric image and the second fabric image are both labeled by manual. Therefore, labeled examples (i.e., the first fabric images and the second fabric images) assist the image classifier in learning the distinguishing of the normal fabric and the fabric containing defects in machine learning process. As described in more detail below, there are several types of fabric defect defined by industrial fabrics association, including netting, smash or hole, soiled filling, float, run, color streak, etc. Therefore, a second fabric image may contain at least one label for indicating at least one defect type. As a result, during the fabric inspection machine being operated to apply a defect inspection treatment to a roll of fabric, the fabric defect recognition system is enabled to screen out defects from the fabric segment by segment.

However, real experience has indicated that, an identical image classifier fails to screen out all types of fabric defect from each type of fabric. In other words, for making a fabric defect recognition system succeed in recognizing all types of fabric defect from each type of fabric, it needs to produce several pre-trained defect recognition models so as to implement the pre-trained defect recognition models into the fabric defect recognition system beforehand. However, a pre-trained defect recognition model is produced by applying a machine learning process to a specific image classifier under using a training dataset including a large quantity of labeled examples. Because the labeled examples are all made by manual, production of the several pre-trained defect recognition models is not easy feat.

According to above descriptions, it is understood that there is still room for improvement in the conventional fabric defect recognition system. In view of this fact, inventors of the present application have made great efforts to make inventive research and eventually provided a defect inspection system having human-machine interaction function.

SUMMARY OF THE INVENTION

The primary objective of the present invention is to disclose a defect inspection system having human-machine interaction function. The defect inspection system includes a linear light source, N number of cameras, a display device, a tag reader, and a modular electronic device. According to the present invention, the linear light source, the cameras and the modular electronic device are used for conducting a defect inspection of an article. On the other hand, the display device, the tag reader and the modular electronic device are adopted for conducting in production of at least one labeled example. Therefore, the modular electronic device can be further configured for applying a machine learning process to an image classifier under using a training dataset containing the labeled examples, thereby producing at least one new defect recognition model or updating the existing defect recognition model.

For achieving the primary objective mentioned above, the present invention provides an embodiment of the defect inspection system having human-machine interaction function, including:

a linear light source, being disposed at a first position for facing a photographing region;

N number of cameras, being disposed at a second position for facing the photographing region, where N is a positive integer;

a display device;

a tag reader; and a modular electronic device, being coupled to the linear light source, the N number of cameras, the display device, and the tag reader, and including a processor, a memory and a human machine interface (HMI), where the memory stores an application program, and the processor being coupled to the memory and the human machine interface;

where the application program includes instructions, such that in case the application program is executed, the processor being configured for:

controlling the linear light source to emit a detection light for irradiating the photographing region during an article being transferred by an article transfer system;

controlling the N number of cameras to acquire an article image frame from the article in case of there being a segment of the article in the photographing region;

applying at least one image process to the article image frame, so as to generate an article feature image;

extracting a plurality of defect features from the article feature image, and then determining whether there are existing any strange defects in the article feature image by matching the plurality of defect features with a plurality of reference defect features;

stopping at least one motor of the article transfer system from running in case of there being one strange defect detected from the article feature image, so as to make the segment of the article be positioned on a manual inspection region;

generating a plurality of defect tags correlated to the strange defect, and controlling the display device to display the plurality of defect tags;

labeling the article feature image so as to produce a labeled example after the tag reader is operated to read a specific defect tag from the plurality of defect tag; and restarting the at least one motor to run after receiving a transfer restarting command transmitted by the human machine interface.

In one embodiment, the tag reader is selected from a group consisting of 2D barcode reader, QR code reader, matrix barcode reader, smart phone, smart glasses, and tablet computer.

In one embodiment, said defect tag is selected from a group consisting of 2D barcode tag, QR code tag, matrix barcode tag, tag containing graphic patterns, tag containing text messages, tag containing alphabets, and tag containing numeric figures.

In one embodiment, the application program consists of a plurality of subprograms, and the plurality of subprograms including:

a first subprogram, being compiled to be integrated in the application program by one type of programming language, and including instructions for configuring the processor to control the linear light source to emit the detection light for irradiating the photographing region;

a second subprogram, being compiled to be integrated in the application program by one type of programming language, and including instructions for configuring the processor to apply the at least one image process to the article image frame for generating the article feature image;

a third subprogram, being compiled to be integrated in the application program by one type of programming language, and including instructions for configuring the processor to extract the plurality of defect features from the article feature image, and to determine whether there are existing any strange defects in the article feature image by matching the plurality of defect features with the plurality of reference defect features;

a fourth subprogram, being compiled to be integrated in the application program by one type of programming language, and including instructions for configuring the processor to stop the at least one motor from running, or to restart the at least one motor to run;

a fifth subprogram, being compiled to be integrated in the application program by one type of programming language, and including instructions for configuring the processor to generate the plurality of defect tags correlated to the strange defect, to control the display device to display the plurality of defect tags, and to produce said labeled example by labeling the article feature image after the tag reader is operated to read said specific defect tag from the plurality of defect tag.

In one embodiment, the processor conducts a plurality of processing steps to produce the plurality of defect tags, and the plurality of processing steps includes:

extracting a plurality of strange defect features from the article feature image;

matching the plurality of strange defect features with the plurality of reference defect features;

correlating the plurality of strange defect features to multiple types of reference article defect; and generate the plurality of defect tags correlated to the multiple types of reference article defect.

In one embodiment, in case the processor fails to correlate the plurality of strange defect features to at least one type of reference article defect, the processor controlling the display device to show a combobox, such that the plurality of strange defect features succeed in being correlated to at least one type of defined article defect after the combobox is operated manually.

In one embodiment, each said camera has a photographic coverage, the N number of cameras have a total photographic coverage, and the total photographic coverage has a first width greater than a second width of the article.

In one embodiment, the plurality of subprograms further including a sixth subprogram, which is compiled to be integrated in the application program by one type of programming language, and includes instructions for configuring the processor to stitching N number of sub-image frames that are transmitted by the N number of cameras to the article image frame.

In one embodiment, the processor stores the labeled example in the memory, and the reference defect features being also stored in the memory.

In one embodiment, the plurality of subprograms further including a seventh subprogram, which is compiled to be integrated in the application program by one type of programming language, and includes instructions for configuring the processor to apply a machine learning process to an image classifier under using a training dataset containing the labeled example, so as to update a first defect recognition model integrated in the third subprogram or produce at least one second defect recognition model for being integrated in the third subprogram.

In a practicable embodiment, the defect inspection system further includes:

at least one rotation speed sensor, being connected to the at least one motor of the article transfer system, and being used for monitoring a rotation speed of said motor.

In one embodiment, after the human machine interface transmits the transfer restarting command to the processor, the processor restarts the at least one motor to run by the rotation speed.

In one embodiment, the N number of cameras acquire the article image frame from the article by a shutter speed, and the shutter speed being positively correlated to a transferring speed of the article.

In one embodiment, the plurality of subprograms further including an eighth subprogram, which is compiled to be integrated in the application program by one type of programming language, and includes instructions for configuring the processor to calculate a displacement of the article based on the rotation speed.

BRIEF DESCRIPTION OF THE DRAWINGS

The invention as well as a preferred mode of use and advantages thereof will be best understood by referring to the following detailed description of an illustrative embodiment in conjunction with the accompanying drawings, where.

DETAILED DESCRIPTION OF THE PREFERRED EMBODIMENTS

To more clearly describe a defect inspection system having human-machine interaction function according to the present invention, embodiments of the present invention will be described in detail with reference to the attached drawings hereinafter.

The present invention discloses a defect inspection system having human-machine interaction function. The defect inspection system includes a linear light source, N number of cameras, a display device, a tag reader, and a modular electronic device. According to the present invention, the linear light source, the cameras and the modular electronic device are used for conducting a defect inspection of an article. On the other hand, the display device, the tag reader and the modular electronic device are adopted for conducting in production of at least one labeled example. Therefore, the modular electronic device is allowed to further apply a machine learning process to an image classifier under using a training dataset containing the labeled examples, thereby producing at least one new defect recognition model or updating the existing defect recognition model.

Figure 1:
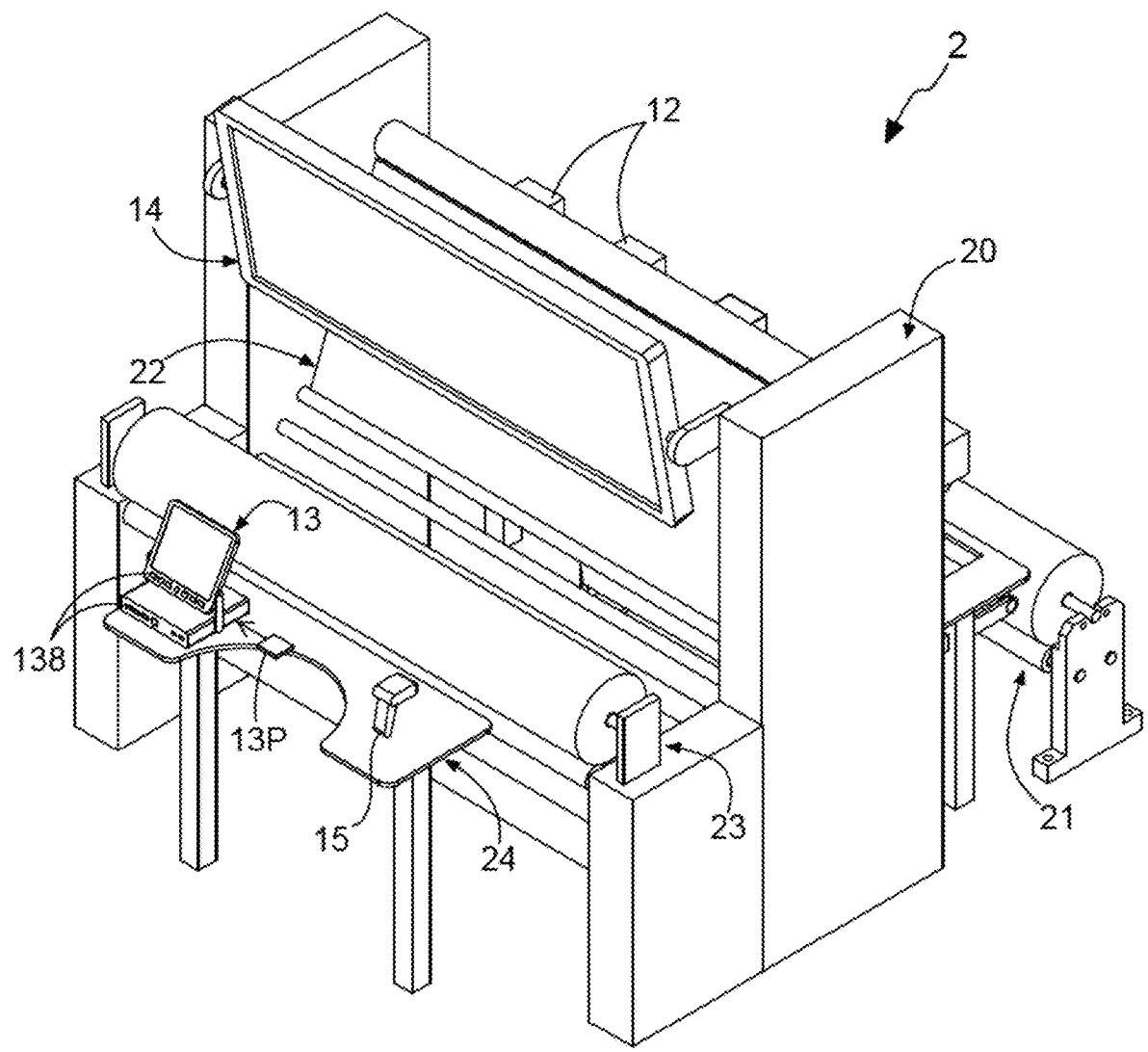
FIG. 1 shows a first stereo diagram of a fabric inspection machine including a defect inspection system according to the present invention.
Figure 2:
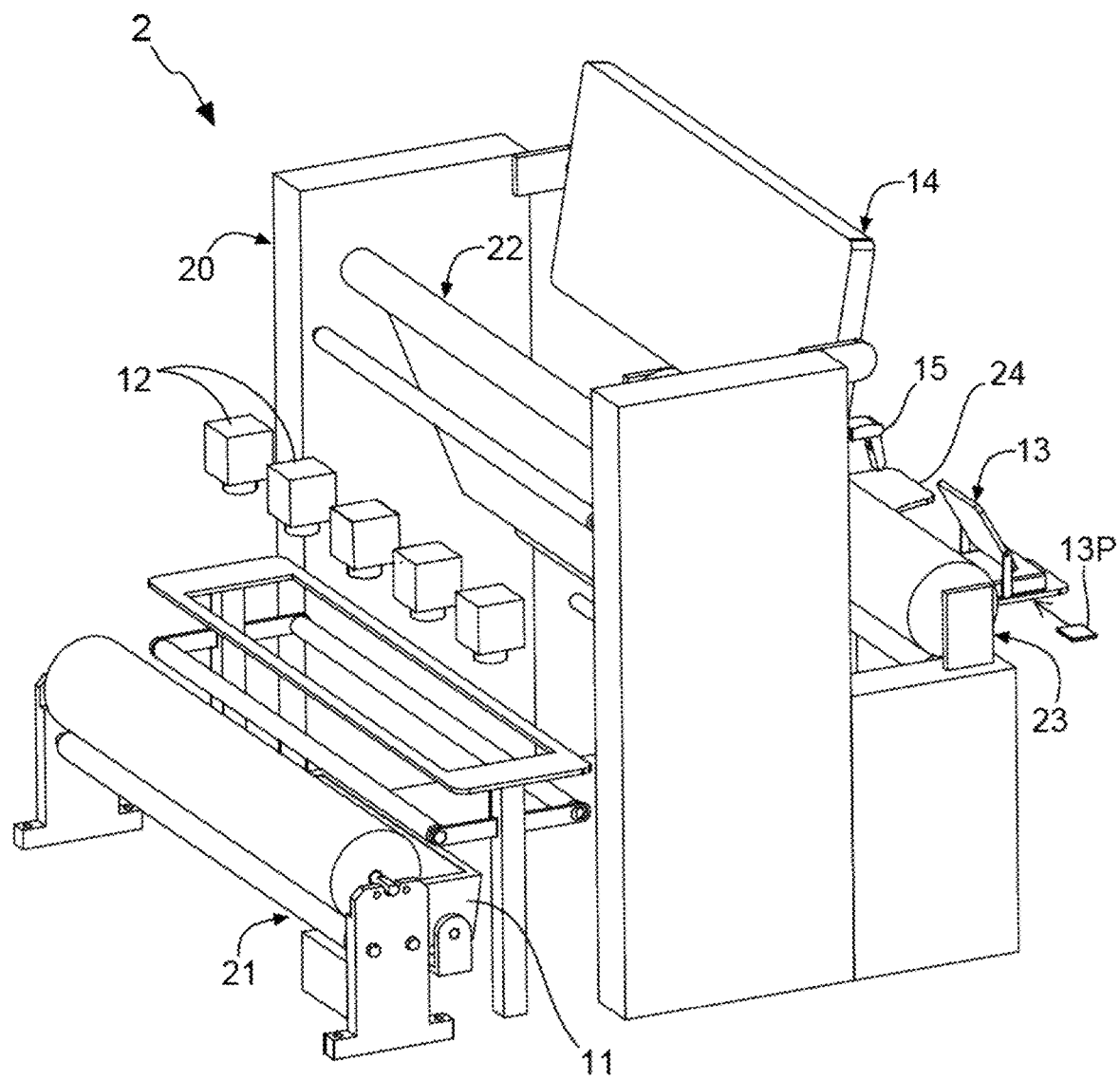
FIG. 2 shows a second stereo diagram of the fabric inspection machine including the defect inspection system according to the present invention.
Figure 3:
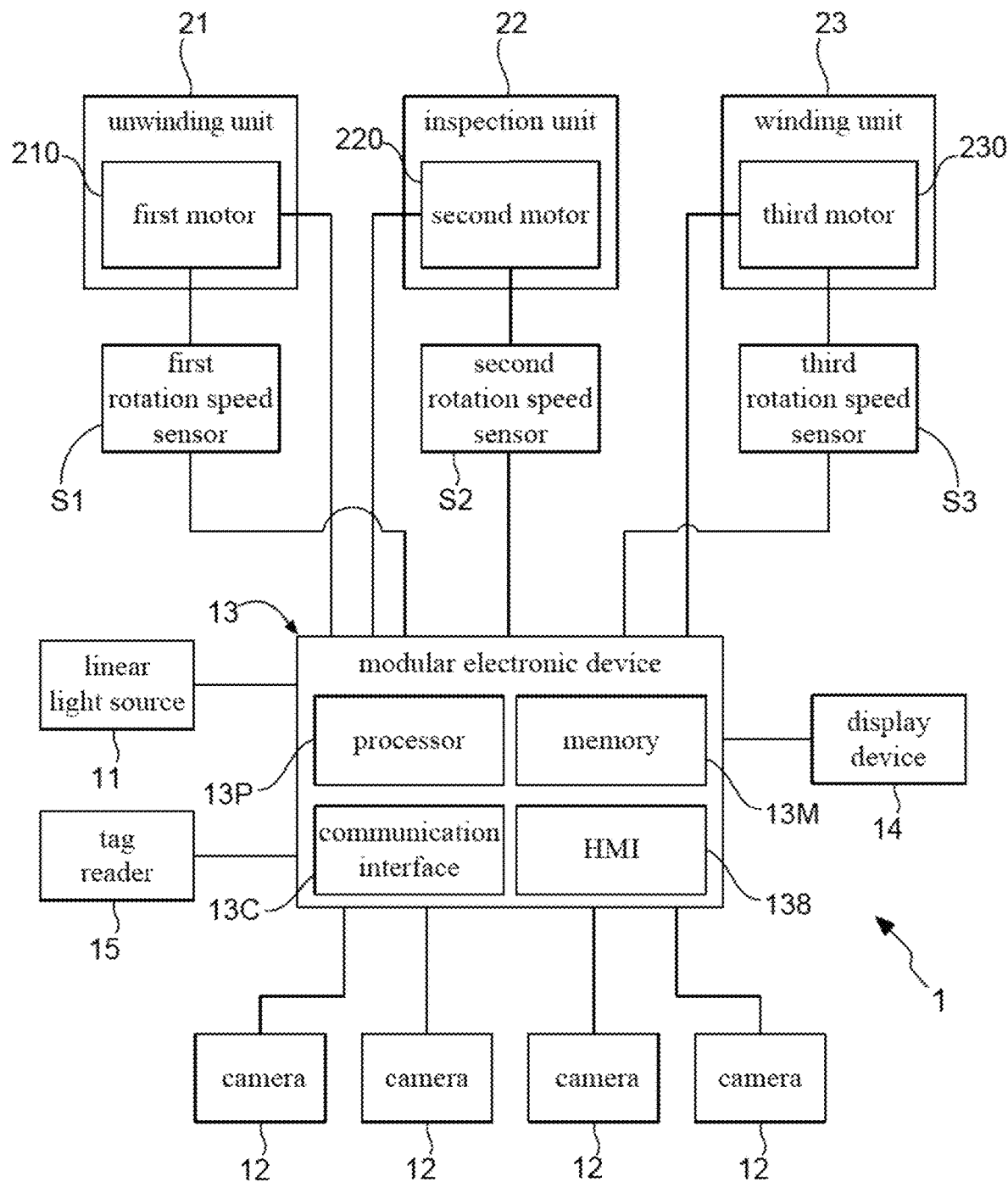
FIG. 3 shows a first block diagram of the defect inspection system according to the present invention.

For example, this defect inspection system can be implemented in a fabric inspection machine. FIG. 1 shows a first stereo diagram of the fabric inspection machine including the defect inspection system according to the present invention. Moreover, FIG. 2 illustrates a second stereo diagram of the fabric inspection machine. As FIG. 1 and FIG. 2 show, the fabric inspection machine 2 includes a machine chassis 20, an unwinding unit 21, an inspection unit 22, a winding unit 23, and an operation table 24. It is understood that, the unwinding unit 21 and the winding unit 23 constitute a roll-to-roll mechanism, which is a fabric transfer system for transferring a test fabric. On the other hand, FIG. 3 shows a first block diagram of the defect inspection system according to the present invention. According to the present invention, the defect inspection system 1 includes: a linear light source 11, N number of cameras 12, a display device 14, a tag reader 15, and a modular electronic device 13, in which the linear light source 11 is disposed at a first position for facing a photographing region, and the N number of cameras 12 are disposed at a second position for facing the photographing region. N is a positive integer.

Figure 4:
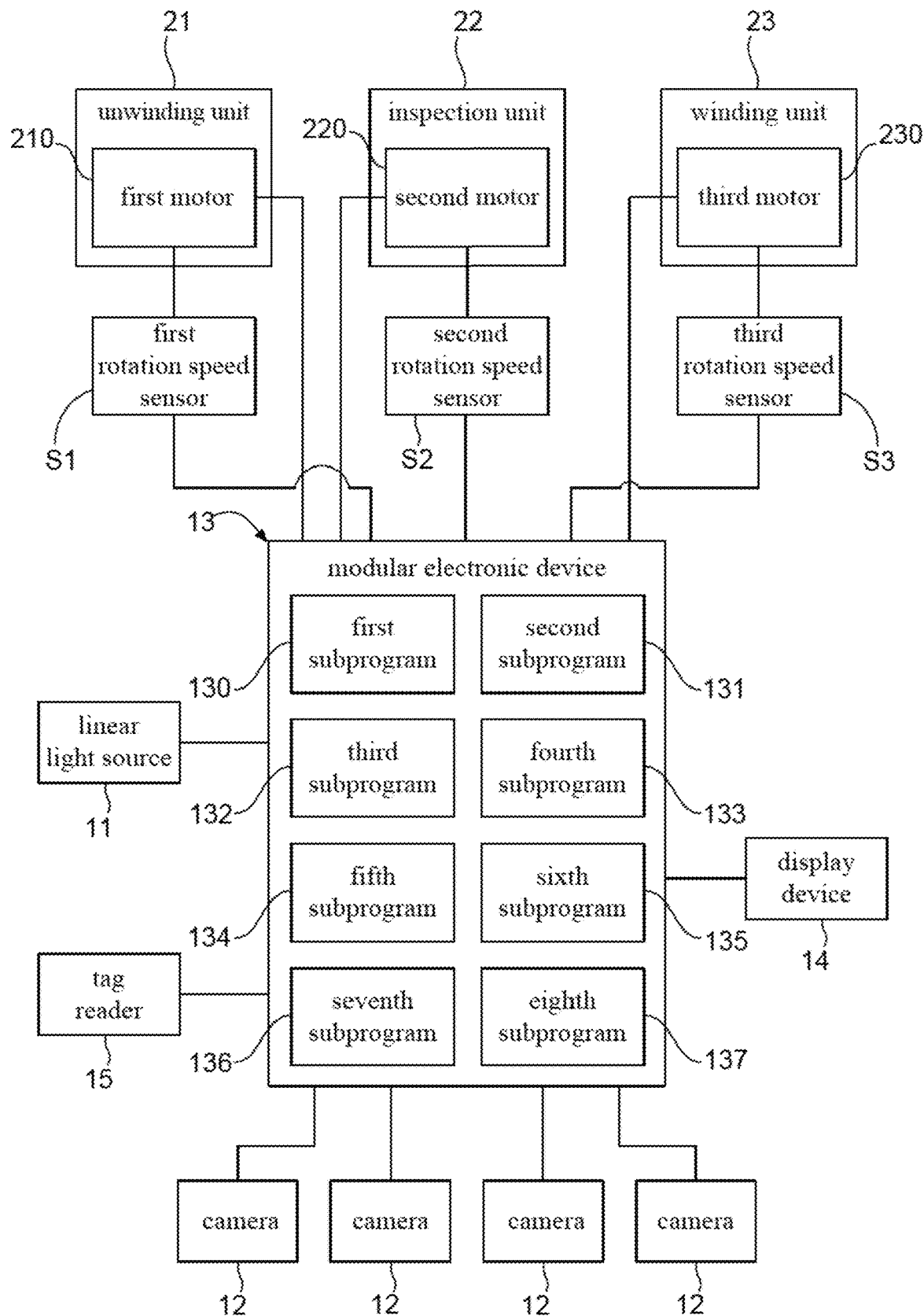
FIG. 4 shows a second block diagram of the defect inspection system according to the present invention.
Figure 5:
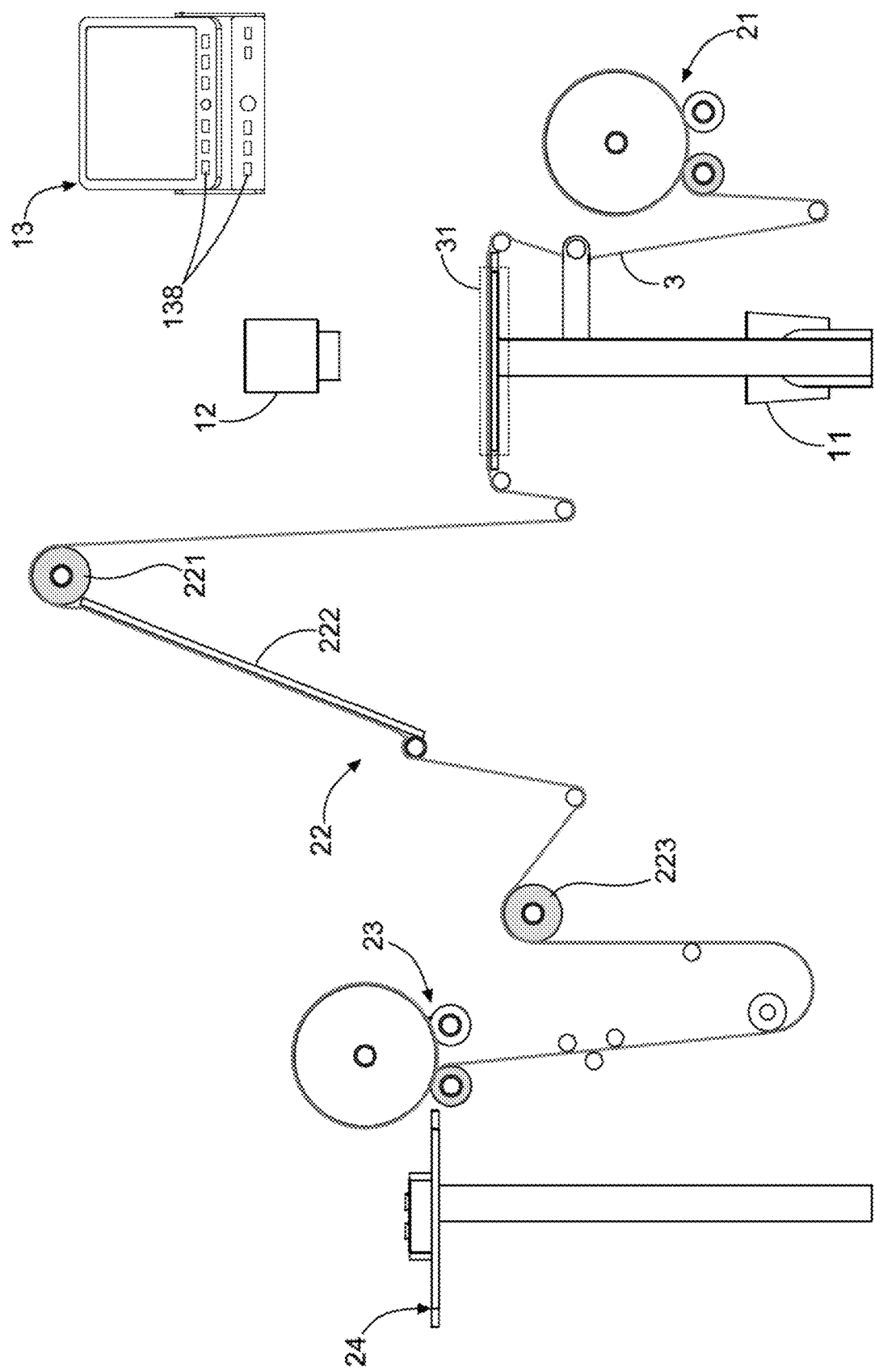
FIG. 5 shows a first side view of an unwinding unit, an inspection unit, a winding unit, and an operation table they are shown in FIG. 1.
Figure 6:
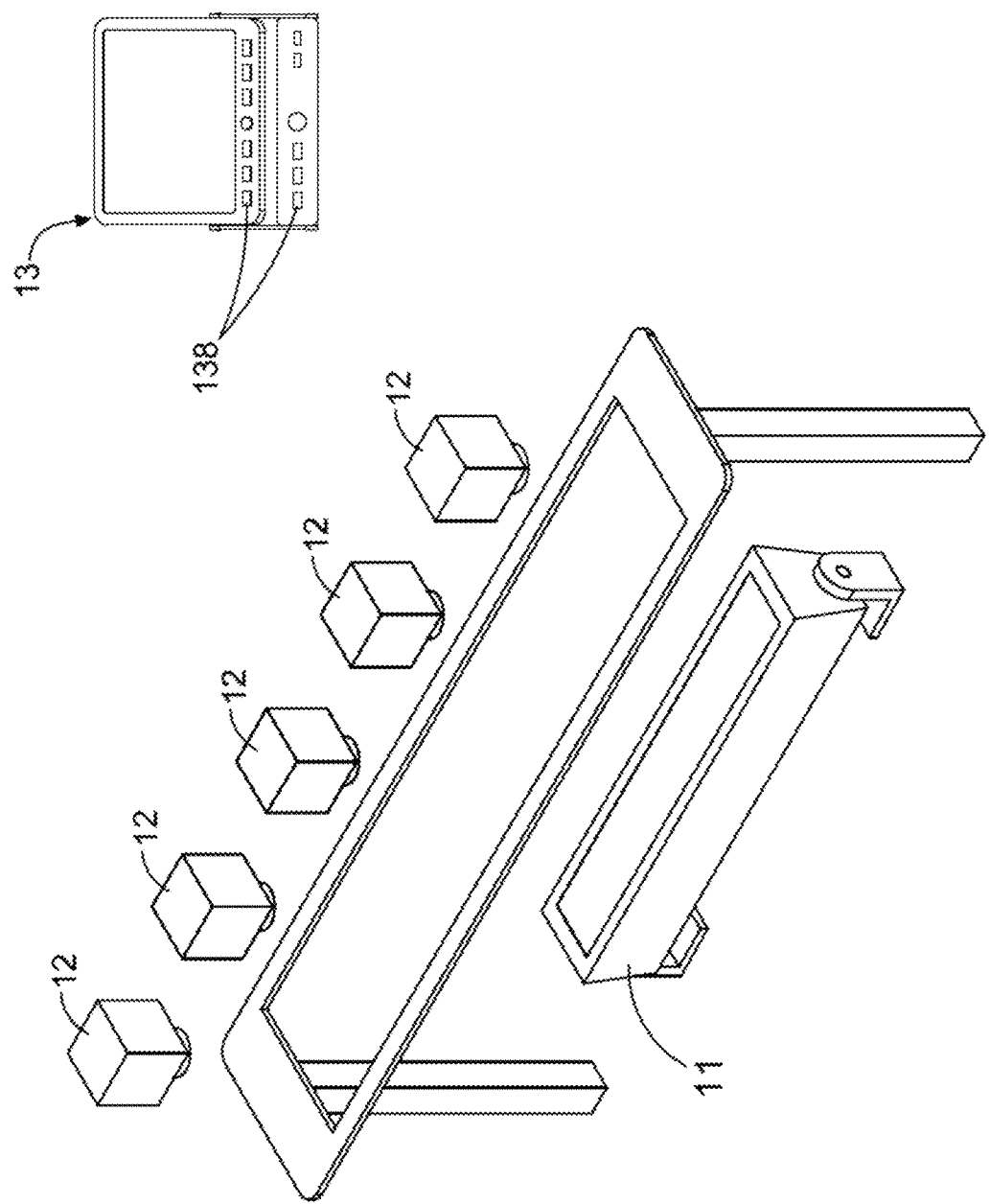
FIG. 6 shows a stereo diagram of a linear light source, N number of cameras, and an inspection unit they are shown in FIG. 1.

Furthermore, FIG. 4 shows a second block diagram of the defect inspection system according to the present invention, and FIG. 5 illustrates a first side view of the unwinding unit 21, the inspection unit 22, the winding unit 23, and the operation table 24 they are shown in FIG. 1. Moreover, FIG. 6 shows a stereo diagram of the linear light source 11, the N number of cameras 12, and the inspection unit 22 they are shown in FIG. 1. As described in more detail below, in the fabric inspection machine 2, the unwinding unit 21 has a first motor 210, the inspection unit 22 has at least one second motor 220, and the winding unit 23 has a third motor 230. When the fabric inspection machine 2 works normally, a roll of an article 3 (i.e., fabric) is wound on a roller of the winding unit 23, and driving the first motor 210 to rotate makes the fabric be discharged by the unwinding unit 21, and then be further transferred to the inspection unit 22.

According to the present invention, the modular electronic device 13 is coupled to the linear light source 11, the N number of cameras 12, the display device 14, and the tag reader 15, and includes a processor 13P, a memory 13M and a human machine interface (HMI) 138. In one practicable embodiment, the modular electronic device 13 is an electronic device coupled to a control box of the fabric inspection machine 2, and the electronic device is selected from a group consisting of industrial computer, desktop computer, laptop computer, and all-in-one computer. In another one practicable embodiment, the modular electronic device 13 can be integrated in a control box of the fabric inspection machine 2.

Particularly, the memory 13M stores an application program, and the processor 13P is coupled to the memory 13M and the HMI 138. By such arrangements, when the defect inspection system 1 works normally, the processor 13P accesses the memory 13M so as to execute the application program, thereby making the processor 13P be configured for conducting a plurality of functions. In one embodiment, the application program includes a first subprogram 130, a second subprogram 131, a third subprogram 132, a fourth subprogram 133, a fifth subprogram 134, a sixth subprogram 135, a seventh subprogram 136, and an eighth subprogram 137, in which the first subprogram 130 is compiled to be integrated in the application program by one type of programming language, and includes instructions for configuring the processor 13P to control the linear light source 11 to emit the detection light for irradiating the photographing region, and to control the N number of cameras 12 to acquire an article image frame from an article 3 (i.e., fabric) in case of there being a segment 31 of the article 3 in the photographing region. In one embodiment, the N number of cameras 12 acquire the article image frame from the article by a shutter speed, and the shutter speed being positively correlated to a transferring speed of the article 3.

On the other hand, the second subprogram 131 is compiled to be integrated in the application program by one type of programming language, and includes instructions for configuring the processor 13P to apply the at least one image process to the article image frame for generating an article feature image. As described in more detail below, the third subprogram 132 is compiled to be integrated in the application program by one type of programming language, and includes instructions for configuring the processor 13P to extract a plurality of defect features from the article feature image, and to determine whether there are existing any strange defects in the article feature image by matching the plurality of defect features with the plurality of reference defect features. Moreover, the fourth subprogram 133 is compiled to be integrated in the application program by one type of programming language, and includes instructions for configuring the processor 13P to stop the at least one motor (i.e., first motor 210, second motor 220 and third motor 230) from running or to restart the at least one motor to run.

In addition, the fifth subprogram 134 is compiled to be integrated in the application program by one type of programming language, and includes instructions for configuring the processor 13P to generate the plurality of defect tags correlated to the strange defect, to control the display device 14 to display the plurality of defect tags, and to produce a labeled example by labeling the article feature image after the tag reader 15 is operated to read said specific defect tag from the plurality of defect tag.

Figure 7:
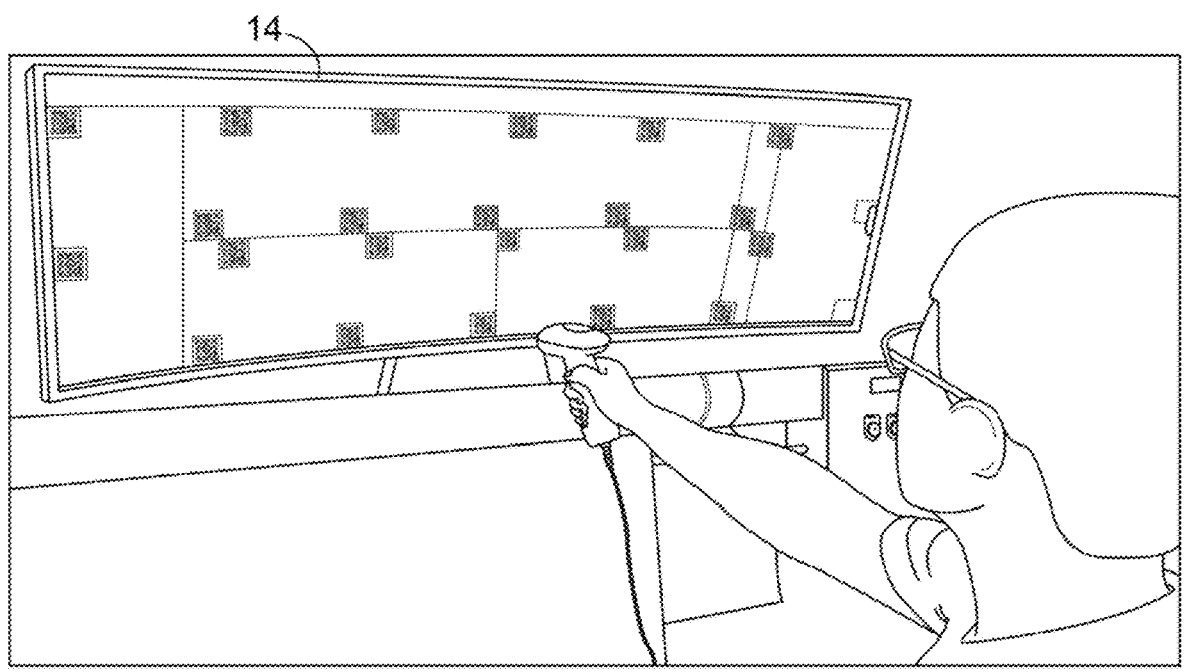
FIG. 7 shows a real photo for describing the human-machine interaction function of the defect inspection system according to the present invention.

By such arrangements, when the fabric inspection machine 2 and the defect inspection system 1 both works normally, the processor 13P accesses the memory 13M so as to execute the application program, and then the processor 13P is configured for conducting a plurality of functions, including:

(a) controlling the linear light source 11 to emit a detection light for irradiating a photographing region in case of the winding unit 21 running to discharge the fabric (i.e., the article 3) by a fabric winding speed;

(b) controlling the N number of cameras 12 to acquire an article image frame from a segment 31 of the fabric in the photographing region;

(c) applying at least one image process to the article image frame, so as to generate an article feature image;

(d) extracting a plurality of defect features from the article feature image, and then determining whether there are existing any strange defects in the article feature image by matching the plurality of defect features with a plurality of reference defect features;

(e) stopping at least one motor (210, 220, 230) from running in case of there being one strange defect detected from the article feature image, so as to make the segment 31 of the fabric (i.e., article 3) be positioned on a manual inspection region (i.e., an inspection platform 222 of the inspection unit 22);

(f) generating a plurality of defect tags correlated to the strange defect, and controlling the display device 14 to display the plurality of defect tags (as FIG. 7 shows);

(g) labeling the article feature image so as to produce a labeled example after the tag reader 15 is operated to read a specific defect tag from the plurality of defect tag; and (h) restarting the at least one motor to run after receiving a transfer restarting command transmitted by the human machine interface.

It needs to further explain that, the processor 13P conducts a plurality of processing steps to produce the plurality of defect tags, and the plurality of processing steps includes:

(f.1) extracting a plurality of strange defect features from the article feature image;

(f.2) matching the plurality of strange defect features with the plurality of reference defect features;

(f.3) correlating the plurality of strange defect features to multiple types of reference article defect; and (f.4) generating the plurality of defect tags correlated to the multiple types of reference article defect.

It is worth further explaining that, in case the processor 13P fails to correlate the plurality of strange defect features to at least one type of reference article defect, the processor 13P controls the display device 14 to show a combobox, such that a domain expert (i.e., a senior inspector) is allowed to operate the combobox by touching the screen of the display device 14, thereby correlating the plurality of strange defect features to at least one type of defined article defect. As a result, the processor 13P stores the labeled example in the memory 13M. Moreover, the reference defect features are also stored in the memory 13M.

In one embodiment, said defect tag can be a 2D barcode tag, a QR code tag, a matrix barcode tag, a tag containing graphic patterns, a tag containing text messages, a tag containing alphabets, or a tag containing numeric figures. For example, FIG. 7 depicts that the defect tag is a QR code tag. Accordingly, the tag reader 15 can be a 2D barcode reader, a QR code reader, a matrix barcode reader, and an electronic device having camera, in which the electronic device can be a smart phone, smart glasses, or a tablet computer.

In addition, as FIG. 1, FIG. 2 and FIG. 7 show, each said camera 12 has a photographic coverage, the N number of cameras 12 have a total photographic coverage, and the total photographic coverage has a first width greater than a second width of the article. Moreover, the plurality of subprograms further including a sixth subprogram 135, which is compiled to be integrated in the application program by one type of programming language, and includes instructions for configuring the processor 13P to stitching N number of sub-image frames that are transmitted by the N number of cameras 12 to the article image frame.

Particularly, as FIG. 4 shows, the plurality of subprograms further including a seventh subprogram 136, which is compiled to be integrated in the application program by one type of programming language, and includes instructions for configuring the processor 13P to apply a machine learning process to an image classifier under using a training dataset containing the labeled example, so as to update a first defect recognition model integrated in the third subprogram 132 or produce at least one second defect recognition model for being integrated in the third subprogram 132. Moreover, in a practicable embodiment, the modular electronic device 13 is able to transmit the labeled example stored in the memory 13M to an external electronic device through the communication interface 13C thereof. Therefore, the external electronic device can also apply a machine learning process to an image classifier under using a training dataset containing the labeled example, so as to produce at least one second defect recognition model for being further integrated in the third subprogram 132.

In a practicable embodiment, said image classifier can be a CNN-based image classifier, a QCNN-based image classifier, a naive Bayes image classifier, a SVM-based image classifier, a SSD-based image classifier, a FCN-based image classifier, a RCNN-based image classifier, FRCNN-based image classifier, a YOLOv1-based image classifier, a YOLOv2-based image classifier, or a YOLOv3-based image classifier.

On the other hand, FIG. 3 and FIG. 4 also depict that the defect inspection system 1 of the present invention further includes a first rotation speed sensor 51, a second rotation speed sensor S2 and a third rotation speed sensor S3, in which the first rotation speed sensor 51 is connected to the first motor 210 for monitoring a first rotation speed of the first motor 210, the second rotation speed sensor S2 is connected to said second motor 220 for monitoring a second rotation speed of said second motor 220, and the third rotation speed sensor S3 is connected to the third motor 230 for monitoring a third rotation speed of the third motor 230. Therefore, after the HMI 138 transmits the transfer restarting command to the processor 13P, the processor 13P restarts the first motor 210, said second motor 220 and the third motor 230 to run by the first rotation speed, the second rotation speed and the third rotation speed, respectively.

Moreover, as FIG. 4 shows, the plurality of subprograms further including an eighth subprogram 137, which is compiled to be integrated in the application program by one type of programming language, and includes instructions for configuring the processor 13P to calculate a displacement of the article 3 based on the first rotation speed, the second rotation speed and the third rotation speed.

Therefore, through above descriptions, all embodiments and their constituting elements of the defect inspection system 1 proposed by the present invention have been introduced completely and clearly; in summary, the present invention includes the advantages of:

(1) This defect inspection system 1 can be implemented into a fabric inspection machine 2. When an inspector operates the fabric inspection machine 2 to conduct a defect inspection treatment of a roll of a fabric (i.e., article 3), the defect inspection system 1 can automatically recognize the most types of detects from the fabric. Moreover, in case of there being at least one strange detect fail to be recognized by the defect inspection system 1, the defect inspection system 1 would show a plurality of defect tags correlated to the strange defect on the display device 14, such that the inspector is allowed to operate a tag reader 15 to read a specific defect tag from the plurality of defect tag. As a result, a labeled example is produced because the article feature image is labeled by the inspector. Subsequently, the modular electronic device 13 of the defect inspection system 1 is allowed to apply a machine learning process to an image classifier under using a training dataset containing the labeled example, thereby producing at least one new defect recognition model or updating the existing defect recognition model.

Moreover, the above description is made on embodiments of the present invention. However, the embodiments are not intended to limit the scope of the present invention, and all equivalent implementations or alterations within the spirit of the present invention still fall within the scope of the present invention.

What is claimed is:

1. A defect inspection system, comprising: a linear light source, being disposed at a first position for facing a photographing region; N number of cameras, being disposed at a second position for facing the photographing region, wherein N is a positive integer; a display device; a tag reader; and a modular electronic device, being coupled to the linear light source, the N number of cameras, the display device, and the tag reader, and comprising a processor, a memory and a human machine interface (HMI), wherein the memory stores an application program, and the processor being coupled to the memory and the human machine interface; wherein the application program includes instructions, such that in case the application program is executed, the processor being configured for: controlling the linear light source to emit a detection light for irradiating the photographing region during an article being transferred by an article transfer system; controlling the N number of cameras to acquire an article image frame from the article in case of there being a segment of the article in the photographing region; applying at least one image process to the article image frame, so as to generate an article feature image; extracting a plurality of defect features from the article feature image, and then determining whether there are existing any strange defects in the article feature image by matching the plurality of defect features with a plurality of reference defect features; stopping at least one motor of the article transfer system from running in case of there being one strange defect detected from the article feature image, so as to make the segment of the article be positioned on a manual inspection region; generating a plurality of defect tags correlated to the strange defect, and controlling the display device to display the plurality of defect tags; labeling the article feature image so as to produce a labeled example after the tag reader is operated to read a specific defect tag from the plurality of defect tags; and restarting the at least one motor to run after receiving a transfer restarting command transmitted by the human machine interface.

2. The defect inspection system of claim 1, wherein the tag reader is selected from a group consisting of 2D barcode reader, QR code reader, matrix barcode reader, smart phone, smart glasses, and tablet computer.

3. The defect inspection system of claim 1, wherein said specific defect tag is selected from a group consisting of 2D barcode tag, QR code tag, matrix barcode tag, tag containing graphic patterns, tag containing text messages, tag containing alphabets, and tag containing numeric figures.

4. The defect inspection system of claim 1, wherein the application program consists of a plurality of subprograms, and the plurality of subprograms comprising: a first subprogram, being compiled to be integrated in the application program by one type of programming language, and including instructions for configuring the processor to control the linear light source to emit the detection light for irradiating the photographing region, and to control the N number of cameras to acquire the article image frame from the article in case of there being a segment of the article in the photographing region; a second subprogram, being compiled to be integrated in the application program by one type of programming language, and including instructions for configuring the processor to apply the at least one image process to the article image frame for generating the article feature image; a third subprogram, being compiled to be integrated in the application program by one type of programming language, and including instructions for configuring the processor to extract the plurality of defect features from the article feature image, and to determine whether there are existing any strange defects in the article feature image by matching the plurality of defect features with the plurality of reference defect features; a fourth subprogram, being compiled to be integrated in the application program by one type of programming language, and including instructions for configuring the processor to stop the at least one motor from running, or to restart the at least one motor to run; a fifth subprogram, being compiled to be integrated in the application program by one type of programming language, and including instructions for configuring the processor to generate the plurality of defect tags correlated to the strange defect, to control the display device to display the plurality of defect tags, and to produce said labeled example by labeling the article feature image after the tag reader is operated to read said specific defect tag from the plurality of defect tags.

5. The defect inspection system of claim 4, wherein the processor conducts a plurality of processing steps to produce the plurality of defect tags, and the plurality of processing steps comprises: extracting a plurality of strange defect features from the article feature image; matching the plurality of strange defect features with the plurality of reference defect features; correlating the plurality of strange defect features to multiple types of reference article defect; and generating the plurality of defect tags correlated to the multiple types of reference article defect.

6. The defect inspection system of claim 5, wherein in case the processor fails to correlate the plurality of strange defect features to at least one type of reference article defect, the processor controlling the display device to show a combo box, such that the plurality of strange defect features succeed in being correlated to at least one type of defined article defect after the combobox is operated manually.

7. The defect inspection system of claim 1, wherein each said camera has a photographic coverage, the N number of cameras having a total photographic coverage, and the total photographic coverage having a first width greater than a second width of the article.

8. The defect inspection system of claim 5, wherein the plurality of subprograms further comprising a sixth subprogram, being compiled to be integrated in the application program by one type of programming language, and including instructions for configuring the processor to stitching N number of sub-image frames that are transmitted by the N number of cameras to the article image frame.

9. The defect inspection system of claim 1, wherein the processor stores the labeled example in the memory, and the reference defect features being also stored in the memory.

10. The defect inspection system of claim 8, wherein the plurality of subprograms further comprising a seventh subprogram, being compiled to be integrated in the application program by one type of programming language, and including instructions for configuring the processor to apply a machine learning process to an image classifier under using a training dataset containing the labeled example, so as to update a first defect recognition model integrated in the third subprogram or produce at least one second defect recognition model for being integrated in the third subprogram.

11. The defect inspection system of claim 1, further comprising: at least one rotation speed sensor, being connected to the at least one motor of the article transfer system, and being used for monitoring a rotation speed of said motor.

12. The defect inspection system of claim 11, wherein after the human machine interface transmits the transfer restarting command to the processor, the processor restarting the at least one motor to run by the rotation speed.

13. The defect inspection system of claim 1, wherein the N number of cameras acquire the article image frame from the article by a shutter speed, and the shutter speed being positively correlated to a transferring speed of the article.

14. The defect inspection system of claim 10, wherein the plurality of subprograms further comprising an eighth subprogram, being compiled to be integrated in the application program by one type of programming language, and including instructions for configuring the processor to calculate a displacement of the article based on the rotation speed.

* * * * *